(12) United States Patent
Holt et al.

(10) Patent No.: US 9,061,097 B2
(45) Date of Patent: Jun. 23, 2015

(54) DRUG DELIVERY DEVICE

(75) Inventors: Mark D. Holt, Moorpark, CA (US); Alexander S. Cairns, Santa Monica, CA (US); Mathias Romacker, Thousand Oaks, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

(21) Appl. No.: 13/155,017

(22) Filed: Jun. 7, 2011

(65) Prior Publication Data

US 2012/0010594 A1 Jan. 12, 2012

Related U.S. Application Data

(60) Provisional application No. 61/352,201, filed on Jun. 7, 2010.

(51) Int. Cl.
*A61K 9/22* (2006.01)
*A61M 5/142* (2006.01)
*A61M 5/158* (2006.01)
(Continued)

(52) U.S. Cl.
CPC ... *A61M 5/14248* (2013.01); *A61M 2005/1583* (2013.01); *A61M 5/326* (2013.01); *A61M 2005/1585* (2013.01); *A61M 5/1452* (2013.01); *A61M 5/148* (2013.01); *A61M 5/1486* (2013.01)

(58) Field of Classification Search
CPC .............. A61M 5/14248; A61M 2005/14252; A61M 2005/1585; A61M 2005/1583; A61M 5/3287
USPC ............... 604/890.1, 131, 134–148
See application file for complete search history.

(56) References Cited

U.S. PATENT DOCUMENTS

| 4,886,499 A | 12/1989 | Cirelli et al. |
| 5,135,479 A | 8/1992 | Sibalis et al. |

(Continued)

FOREIGN PATENT DOCUMENTS

| CN | 1476566 A | 2/2004 |
| CN | 1747683 A | 3/2006 |

(Continued)

OTHER PUBLICATIONS

Thompson, "Market Trends: Disposable Mono-dose Auto-injectors and Pen-injectors", *Drug Delivery Report*, pp. 53-55 (Winter 2007/2008).

(Continued)

*Primary Examiner* — Emily Schmidt
(74) *Attorney, Agent, or Firm* — Marshall, Gerstein & Borun LLP

(57) ABSTRACT

A drug delivery device includes a housing having an interior space, a needle having retracted and deployed states, an injector to move the needle between retracted and deployed states, and a reservoir disposed within the interior space, the reservoir configured to receive a volume of a drug and to be in fluid communication with the needle. The drug delivery device also includes a controller coupled to the injector and the reservoir, and configured to actuate the injector to move the needle from the retracted state to the deployed state only once, and to actuate the reservoir to deliver the volume of the drug to the patient as a single bolus after a preselected time period has elapsed, the controller disposed within the interior space and configured prior to being disposed within the interior space. The delivery device is wearable, disposable, and single-use.

42 Claims, 3 Drawing Sheets

(51) Int. Cl.
  *A61M 5/32* (2006.01)
  *A61M 5/145* (2006.01)
  *A61M 5/148* (2006.01)

(56) References Cited

U.S. PATENT DOCUMENTS

| | | | |
|---|---|---|---|
| 5,250,023 A | 10/1993 | Lee et al. | |
| 5,527,288 A | 6/1996 | Gross et al. | |
| 5,693,016 A | 12/1997 | Gumaste et al. | |
| 5,782,799 A | 7/1998 | Jacobsen et al. | |
| 5,785,688 A | 7/1998 | Joshi et al. | |
| 5,814,020 A | 9/1998 | Gross | |
| 5,820,622 A | 10/1998 | Gross et al. | |
| 5,858,001 A | 1/1999 | Tsals et al. | |
| 5,860,957 A | 1/1999 | Jacobsen et al. | |
| 5,957,895 A | 9/1999 | Sage et al. | |
| 5,997,501 A | 12/1999 | Gross et al. | |
| 6,010,492 A | 1/2000 | Jacobsen et al. | |
| 6,068,613 A | 5/2000 | Kriesel et al. | |
| 6,074,369 A | 6/2000 | Sage et al. | |
| 6,126,637 A | 10/2000 | Kriesel et al. | |
| 6,186,982 B1 | 2/2001 | Gross et al. | |
| 6,387,078 B1 | 5/2002 | Gillespie, III | |
| 6,485,461 B1 | 11/2002 | Mason et al. | |
| 6,530,900 B1 | 3/2003 | Sahar et al. | |
| 6,589,229 B1 | 7/2003 | Connelly et al. | |
| 6,595,956 B1 | 7/2003 | Gross et al. | |
| 6,635,049 B1 | 10/2003 | Robinson et al. | |
| 6,656,158 B2 | 12/2003 | Gregory et al. | |
| 6,656,159 B2 | 12/2003 | Flaherty | |
| 6,669,669 B2 | 12/2003 | Flaherty et al. | |
| 6,692,457 B2 | 2/2004 | Flaherty | |
| 6,699,218 B2 | 3/2004 | Flaherty et al. | |
| 6,702,779 B2 | 3/2004 | Connelly et al. | |
| 6,723,072 B2 | 4/2004 | Flaherty et al. | |
| 6,740,059 B2 | 5/2004 | Flaherty | |
| 6,749,587 B2 | 6/2004 | Flaherty | |
| 6,768,425 B2 | 7/2004 | Flaherty et al. | |
| 6,824,529 B2 | 11/2004 | Gross et al. | |
| 6,830,558 B2 | 12/2004 | Flaherty et al. | |
| 6,953,446 B2 | 10/2005 | Fischer | |
| 6,955,670 B2 | 10/2005 | Martin et al. | |
| 6,960,192 B1 | 11/2005 | Flaherty et al. | |
| 7,014,625 B2 | 3/2006 | Bengtsson | |
| 7,018,360 B2 | 3/2006 | Flaherty et al. | |
| 7,029,455 B2 | 4/2006 | Flaherty | |
| 7,070,580 B2 | 7/2006 | Nielsen | |
| 7,115,108 B2 | 10/2006 | Wilkinson et al. | |
| 7,128,727 B2 | 10/2006 | Flaherty et al. | |
| 7,137,964 B2 | 11/2006 | Flaherty | |
| 7,137,965 B2 | 11/2006 | Fischer et al. | |
| 7,144,384 B2 | 12/2006 | Gorman et al. | |
| 7,303,549 B2 | 12/2007 | Flaherty et al. | |
| 7,410,476 B2 | 8/2008 | Wilkinson et al. | |
| 7,524,304 B2 | 4/2009 | Genosar | |
| 7,530,964 B2 | 5/2009 | Lavi et al. | |
| 7,537,590 B2 | 5/2009 | Santini, Jr. et al. | |
| 2002/0040208 A1 | 4/2002 | Flaherty et al. | |
| 2002/0151875 A1 | 10/2002 | Haller | |
| 2003/0014014 A1 | 1/2003 | Nitzan | |
| 2003/0055380 A1 | 3/2003 | Flaherty | |
| 2004/0010207 A1 | 1/2004 | Flaherty et al. | |
| 2004/0015042 A1* | 1/2004 | Vincent et al. | 600/17 |
| 2004/0054327 A1 | 3/2004 | Gillespie | |
| 2004/0068224 A1 | 4/2004 | Couvillon et al. | |
| 2004/0078028 A1 | 4/2004 | Flaherty et al. | |
| 2004/0092865 A1 | 5/2004 | Flaherty et al. | |
| 2004/0092878 A1 | 5/2004 | Flaherty | |
| 2004/0116866 A1 | 6/2004 | Gorman et al. | |
| 2004/0204673 A1 | 10/2004 | Flaherty | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0022274 A1 | 1/2005 | Campbell et al. | |
| 2005/0182366 A1 | 8/2005 | Vogt et al. | |
| 2005/0203461 A1* | 9/2005 | Flaherty et al. | 604/131 |
| 2005/0234430 A1 | 10/2005 | Mao et al. | |
| 2006/0178629 A1 | 8/2006 | Gillespie et al. | |
| 2006/0178631 A1 | 8/2006 | Gillespie et al. | |
| 2006/0178642 A1 | 8/2006 | Gillespie et al. | |
| 2006/0276771 A1 | 12/2006 | Galley et al. | |
| 2007/0078394 A1 | 4/2007 | Gillespie, III | |
| 2007/0118405 A1 | 5/2007 | Campbell et al. | |
| 2007/0135767 A1 | 6/2007 | Gillespie et al. | |
| 2008/0051738 A1* | 2/2008 | Griffin | 604/273 |
| 2008/0220092 A1 | 9/2008 | Dipierro et al. | |
| 2009/0093792 A1 | 4/2009 | Gross et al. | |
| 2009/0093793 A1 | 4/2009 | Gross et al. | |
| 2010/0227818 A1* | 9/2010 | Bock et al. | 514/12 |
| 2012/0022499 A1* | 1/2012 | Anderson et al. | 604/506 |

FOREIGN PATENT DOCUMENTS

| | | |
|---|---|---|
| CN | 101238468 A | 8/2008 |
| WO | WO 01/58506 | 8/2001 |
| WO | WO 02/40083 | 5/2002 |
| WO | WO 2005/039685 | 5/2005 |
| WO | WO 2006/121921 | 11/2006 |
| WO | WO 2007/010522 | 1/2007 |
| WO | WO 2007/129317 | 11/2007 |

OTHER PUBLICATIONS

International Search Report and Written Opinion from corresponding International application No. PCT/US2011/039444, dated Oct. 6, 2011 (8 pp.).

* cited by examiner

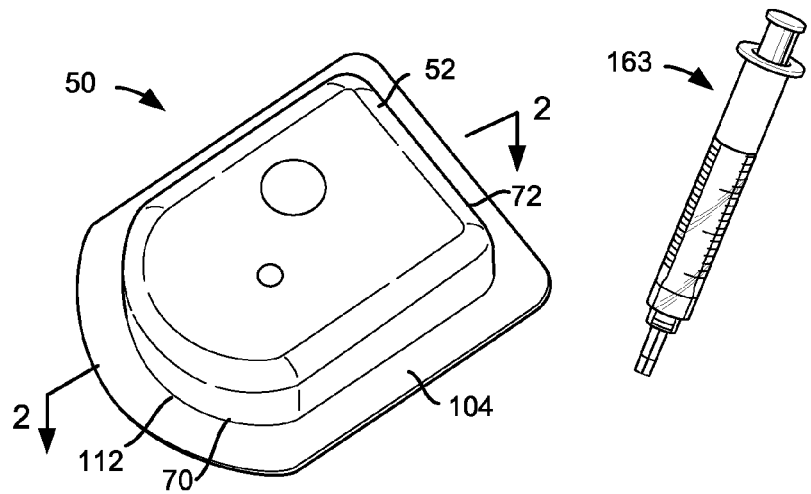
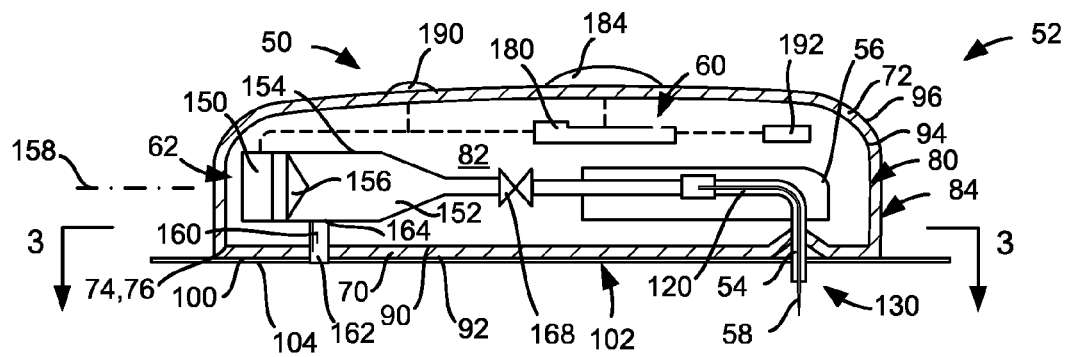
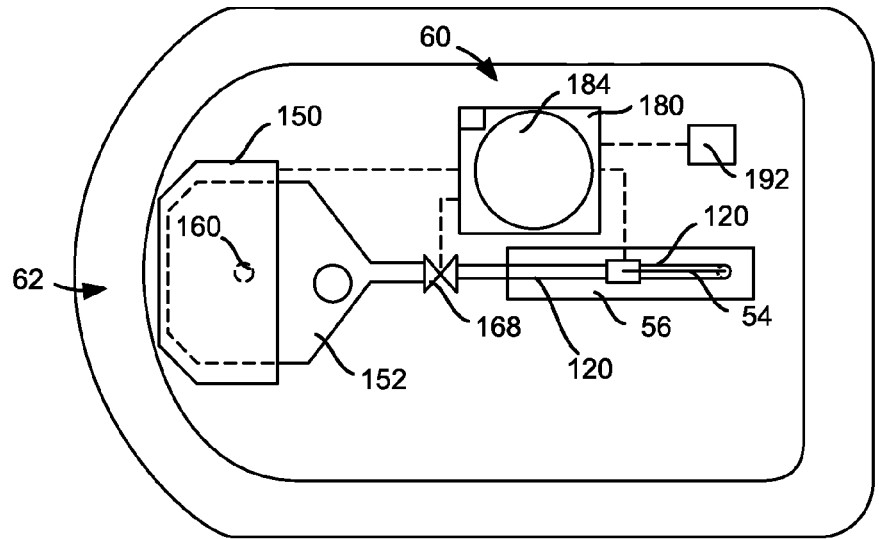

DRUG DELIVERY DEVICE

This application claims the benefit of U.S. Application No. 61/352,201, filed Jun. 7, 2010, which is hereby incorporated by reference in its entirety herein.

BACKGROUND

This patent is directed to drug delivery devices, and in particular to a single-use, disposable drug delivery device.

Injectable drugs are conventionally administered through the use of a needle attached to a syringe. The needle is inserted to the appropriate depth (e.g., subcutaneous, intradermal, or intramuscular), and the plunger is moved within the cylinder to eject the drug from the cylinder into the patient. Many times, the patient will be required to self-administer a drug, in which case the patient is responsible for filling the syringe with the drug, and then injecting the drug into themselves.

When dealing with a disease, such as diabetes, a patient may have to administer a series of injections throughout the course of the day. For example, the patient may have to administer a number of fast-acting insulin injections before meals, as well as a long-acting insulin injection before bedtime. There are issues that can arise when this many injections are administered in a day, including the potential for the patient to lose track of or forget to administer one or more of the injections.

To address the issues posed by having to self-administer a series of injections throughout the day, patients often resort to pumps or automatic injection devices to eliminate the need to manually keep track of the injections. These pumps may be implanted surgically, although certain autoinjectors are designed to be strapped on or attached externally to the patient. The pump or automatic injector may have a microprocessor that follows an internal program to administer a drug (e.g., insulin) to the patient throughout the course of the day. Typically, at least the control portion of the pump or injector is intended to be reused, and often is detachable from the portions of the system that are injected into the patient.

As set forth in more detail below, the present disclosure sets forth a drug delivery device embodying advantageous alternatives to the conventional devices discussed above, which drug delivery device can be a disposable, single-use drug delivery device.

SUMMARY

In an aspect of the present disclosure, a drug delivery device includes a disposable housing having an interior surface defining an interior space and an exterior surface, a needle having a retracted state wherein the needle is withdrawn inside of the interior space and a deployed state wherein a pointed end of the needle projects beyond the exterior surface of the housing, an injector coupled to the needle to move the needle between the retracted and deployed states, and a reservoir disposed within the interior space, the reservoir configured to receive a volume of a drug and to be in fluid communication with the needle. The drug delivery device also includes a controller coupled to the injector and the reservoir, the controller being configured to actuate the injector to move the needle from the retracted state to the deployed state only once, and to actuate the reservoir to deliver the volume of the drug to the patient as a single bolus after a preselected time period has elapsed, the controller disposed within the interior space and configured prior to being disposed within the interior space. Further, the delivery device is wearable, disposable, and single-use.

In another aspect of the present disclosure, a method of operation of a wearable, disposable, single-use drug delivery device is provided. The method includes automatically injecting a pointed end of a needle from an interior space defined in a housing of the delivery device into the patient to define an injection site only once according to a controller contained within the interior space. The method also includes automatically actuating a reservoir to deliver a volume of a drug to the patient through the injection site as a single bolus after a preselected time period has elapsed according to the controller contained within the interior space.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 1 is a perspective view of a drug delivery device according to an embodiment of the present disclosure, with an associated syringe which may be used to fill the device;

FIG. 2 is a cross-sectional view of the drug delivery device of FIG. 1 taken along line 2-2;

FIG. 3 is a cross-sectional view of the drug delivery device of FIG. 2 taken along line 3-3;

DETAILED DESCRIPTION OF VARIOUS EMBODIMENTS

Figure 4:
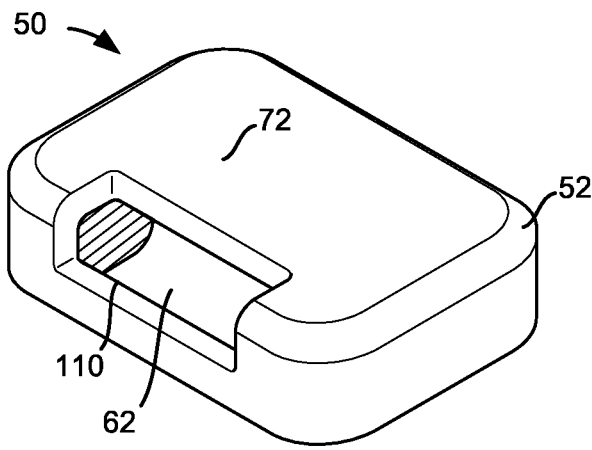
FIG. 4 is a perspective view of a variant of the drug delivery device of FIG. 1, including an observation window.

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

FIGS. 1-3 illustrate a wearable, disposable, single-use drug delivery device 50. The device 50 has a disposable housing 52 that may be attached to a patient or wearer with adhesive, for example. As seen in FIGS. 2 and 3, a needle 54 and injector 56 are disposed in the housing 52, with the needle 54 having a retracted state wherein a pointed end 58 (in fact, the entire needle 54) may be withdrawn inside the housing 52 and a deployed state wherein the pointed end 58 projects from the housing 52 (see FIGS. 5-8), the injector 56 moving the needle 54 from the retracted state to the deployed state. The device 50 also includes a controller 60 that is coupled to the injector 56 and a drug supply 62 containing a volume of a drug, the controller 60 operating the injector 56 to move the needle 54 and the drug supply 62 to deliver the volume of the drug.

The drug delivery device 50 is particularly well suited for use in addressing a particular issue for patients undergoing chemotherapy for the treatment of cancer, although it may have uses outside this particular application. Chemotherapy agents, such as fludarabine, mitoxantrone, and cyclophosphamide, work in different ways to stop the growth of cancer cells. Some agents act to kill the cancer cells, while other agents work to stop the cancer cells from dividing. Administration of more than one agent at a time may enhance the effectiveness of the therapy.

At the same time that these chemotherapy agents are working on the cancerous cells, they may have the side effect of suppressing the patient's immune system. To counter the effects of the chemotherapy agents on the immune system, colony stimulating factors, such as G-CSF, may be administered to increase the number of immune cells (e.g., white blood cells) found in bone marrow or peripheral blood. Such G-CSF agents include, but are not limited to, Neupogen® (filgrastim) and Neulasta® (pegfilgrastim). However, conventional thinking suggests that for the G-CSF to be effective, the G-CSF should not be administered during the administration of the chemotherapy agents, even to the extent that administration of the G-CSF should come at least twenty-four hours after the administration of the last dose of the chemotherapy agents. As a consequence, the patient must return to a treatment location, for example the doctor's office, for a separate appointment to receive the injection of G-CSF.

In various other embodiments, the drug delivery device may be used with various pharmaceutical products, which use may or may not occur under the same conditions as described above for G-CSF. These products may include, for example, an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing Publication;

Myostatin binding proteins, peptibodies, and related proteins, and the like, including myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/03742 and in US Publ. No. 2005/112694, which are incorporated herein by reference in there entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in US Publ. No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R- binding fragments and derivatives thereof, each of which is individually and specifically incorporated by reference herein in its entirety fully as disclosed in the foregoing International Publication;

Also among non-limiting examples of anti-IGF-1R antibodies for use in the methods and compositions of the present invention are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J Biol. Chem. 279:2856-65, including but not limited to antibodies 2F8, A12, and IMC-A12 as described therein;

(iii) PCT Publ. No. WO 07/012,614 (published Feb. 1, 2007), WO 07/000,328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751, 871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011,941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication;

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in US Publ. No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and US Publ. No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. application Ser. No. 11/068,289, which is incorporated herein by reference in its entirety, particularly in parts pertinent to proteins that bind OX40L and/or other ligands of the OXO40 receptor; and Other exemplary proteins, including Activase® (alteplase, tPA); Aranesp® (darbepoetin alfa); Epogen® (epoetin alfa, or erythropoietin); Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP llb/Ilia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

According to the present disclosure, a method of operation of the device 50 described above addresses this issue where a single bolus must be applied at a particular time after a particular procedure. The device 50 adheres to the skin of a patient, most likely, but not exclusively, after being placed there by healthcare personnel associated with the procedure. The device 50 automatically injects the pointed end 58 of the needle 54 from an interior (potentially sealed) space defined by the housing 52 of the delivery device 50 into the patient to define an injection site only once according to the configuration of the controller 60 contained within the space. Additionally, the device 50 may automatically determine that a preselected time period has elapsed only once according to the configuration of the controller 60, the controller 60 being configured to determine the preselected time before the controller 60 is disposed in the space. Further, the device 50 automatically actuates a drug supply 62 to deliver a volume of a drug to the patient through the injection site as a single bolus according to the configuration of the controller 60. According to those embodiments wherein the controller 60 is defined by a microprocessor or the like, the configuration of the controller 60 may correspond to the programming of the controller.

As a consequence of the use of such a device 50, the patient would not be required to return to the healthcare provider for a visit simply for receipt of a single injection. This has benefits for the patient, in that the patient is not required to return to the healthcare provider and therefore can proceed with the healing process without further immediate return visits. This also has benefits for the healthcare provider in that they can remotely control the injection with certainty as to the issue of timing, permitting resources that would otherwise be tasked for the return visit to instead be used for the healthcare of other patients.

Having thus described the device 50 and its use in general terms, the structure and operation of the device 50 is now described in greater detail. FIG. 1 illustrates the disposable housing 52. The disposable housing 52 may be made of a plastic material. As seen in FIG. 2, the housing 52 may be defined by two sections, a plate 70 that is applied against the wearer's skin, and a dome 72 that is attached to the plate 70, preferably by a seal at an interface between a peripheral edge 74 of the plate 70 and a peripheral edge 76 of the dome 72.

As shown in FIG. 2, the housing 52 has an interior surface 80 defining an interior space 82 and an exterior surface 84. In particular, the plate 70 has an interior surface 90 and an exterior surface 92, and the dome 72 has an interior surface 94 and an exterior surface 96. According to the illustrated embodiment, the interior surface 80 of the housing 52 is defined by the interior surfaces 90, 94 of the plate 70 and the dome 72, while the exterior surface 84 of the housing 52 is defined by the exterior surfaces 92, 96 of the plate 70 and dome 72.

As noted above, the housing 52 may be attached to the skin of the wearer. In particular, an adhesive may be used. The adhesive may be adapted to releasably secure the housing to skin during a single application. As shown in FIG. 2, the adhesive is disposed in a layer 100 on a portion 102 of the exterior surface 84 of the housing 52, and in particular on the exterior surface 92 of the plate 70. The adhesive is covered with a removable, disposable sheet 104 prior to application of the housing 52 to the skin of the wearer.

As is illustrated in FIG. 4, the housing 52 may have an inspection window 110 formed therethrough that allows the healthcare provider or the patient to view the drug supply 62. The inspection window 110 illustrated in FIG. 4 is formed in the dome 72 of the housing 52, although it could instead be formed in the plate 70 or in the dome 72 and the plate 70 depending on placement of a parting line 112 (see FIG. 1) between the dome 72 and the plate 70. The inspection window 110 may permit visual inspection for any one or more of the following reasons: for assurance that the device 50 has been filled/filled properly prior to activation of the device 50; for inspection of the drug to ensure quality; and for confirmation that the drug is being/has been delivered to the patient.

As noted above, the device 50 may include a needle 54 with a pointed end 58. The needle 54 has a retracted state wherein the pointed end 58 of the needle 54 is withdrawn inside of the space 82 defined by the housing 52; in fact, according to certain embodiments such as that illustrated herein, the entire needle 54 is withdrawn inside of the space 82 in the retracted state. The needle 54 also has a deployed state (illustrated in FIG. 2) wherein the pointed end 58 of the needle 54 projects from the space 82 beyond the exterior surface 84 of the housing 52 into an injection site of the patient. The needle 54 may be used in conjunction with a catheter 120, the needle 54 being used to insert the catheter 120 into the patient through the injection site, and the drug passing through the catheter 120 into the patient during administration. Phrased slightly differently, the device 50 may, according to certain embodiments, automatically insert a soft cannula into the subcutaneous tissue. However, the benefits of using a needle 54 alone include lower susceptibility to obstructions in the flow path from the drug supply 62 to the patient, more accurate injection depth and location, and avoidance of any negative perceptions that healthcare providers or patients may have regarding catheters.

As illustrated in FIGS. 2 and 5-8, the housing 52 (specifically the plate 70) may have an aperture or opening 130 formed therein to permit the needle 54 (and catheter 120) to pass therethrough. According to certain embodiments (e.g., FIG. 2), the aperture 130 may be unobstructed, such that there is no impediment or obstacle to the movement of the needle 54 (and catheter 120) through the opening 130. However, to better maintain the sterility of the needle 54 and the device's container closure integrity (CCI), a septum 132 (shown in FIG. 5) or a shield 134 (shown in FIG. 7) may be disposed in or over the aperture 130, or within the space 82 defined by the housing 52 so as to overlie the opening 130, as in FIGS. 5-8.

Figure 5:
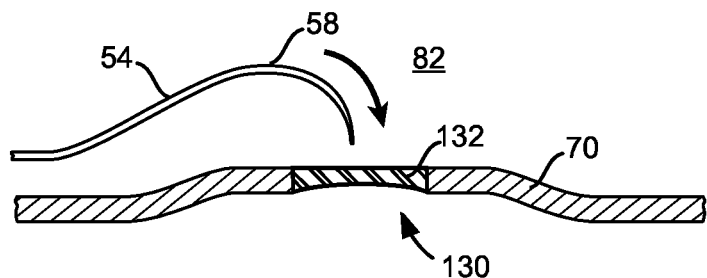
FIG. 5 is an enlarged, fragmentary, cross-sectional view of a barrier system used in conjunction with a needle according to the present disclosure, with the needle in a retracted state.
Figure 6:
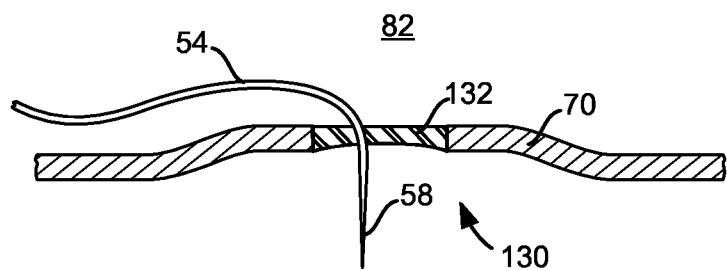
FIG. 6 is an enlarged, fragmentary, cross-sectional view of the barrier system of FIG. 5, with the needle in a deployed state.

FIGS. 5 and 6 illustrate a variant wherein a septum 132, which may be made of a rubber, is included. The septum 132 is disposed between the needle 54 (and the space 82) and the patient's skin with the needle 54 in the retracted state (FIG. 5). In the deployed state (FIG. 6), at least a portion of the needle 54 (i.e., the pointed end 58) will depend from the space 82 through the septum 132. As such, the septum 132 is always present as a barrier between the interior space 82 and the external environment.

Figure 7:
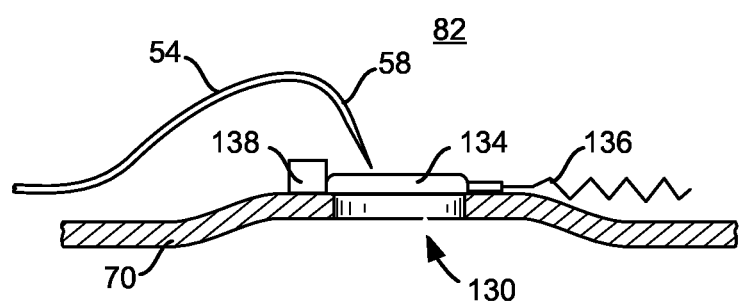
FIG. 7 is an enlarged, fragmentary, cross-sectional view of a variant barrier system used in conjunction with a needle according to the present disclosure, with the needle in a retracted state.
Figure 8:
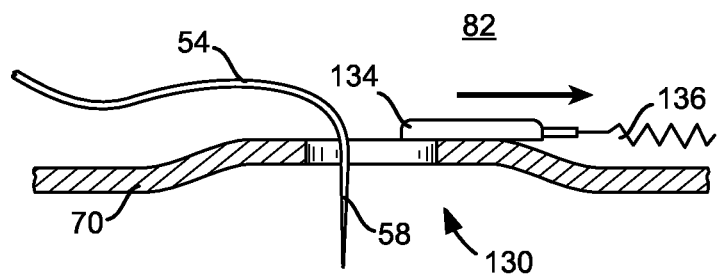
FIG. 8 is an enlarged, fragmentary, cross-sectional view of the barrier system of FIG. 7, with the needle in a deployed state.

FIGS. 7 and 8 illustrate a variant wherein a shield 134, which may be made of a rigid material or a flexible material, is included. The shield 134, like the septum 132, is disposed between the needle 54 (and the space 82) and the patient's skin with the needle 54 in the retracted state (FIG. 7). In the deployed state (FIG. 8), however, the shield 134 must be moved out of the path of the needle 54 prior to the insertion of the needle 54 (and catheter 120) into the patient. For example, a spring 136 may be attached to the shield 134 to bias the shield 134 toward its retracted state. The controller 60 may open a latch 138 that cooperates with the shield 134 to maintain the shield 134 in its unretracted state, whereupon the shield 134 moves to the retracted state in accordance with the biasing force applied by the spring 136. Other mechanisms are also possible.

The device includes the injector 56 (FIG. 3). The injector 56 is coupled to the needle 54 to move the needle 54 between the retracted and deployed states. Examples of exemplary injectors may be found in U.S. Pat. Nos. 7,144,384 and 7,128,727, which patents are incorporated by reference herein for all purposes.

As shown in FIG. 2, a drug supply 62 is also disposed within the space 82 and in fluid communication with the needle 54; preferably, the drug supply 62 is in selective or controllable fluid communication with the needle 54. The drug supply 62 contains a volume of a drug. According to certain embodiments, the drug may be a granulocyte colony-stimulating factor (G-CSF) or a pegylated G-CSF or any other desired pharmaceutical. For example, the pharmaceutical may be an erythropoiesis stimulating agent, a TNF blocker, interleukin receptor specific antibody, IGF-receptor specific antibody or TGF-specific antibody.

According to the illustrated embodiment, the drug supply 62 may include a pump 150 and a reservoir 152 (FIGS. 2 and 3). According to an embodiment of the present disclosure, the reservoir 152 and pump 150 may be defined in part by a combination of a rigid-walled cylinder 154 and a plunger 156 fitted to move along a longitudinal axis 158 of the cylinder 154 (FIG. 2). The movement of the plunger 156 may be caused by the operation of a gear train that is connected to a motor, according to one variant. Other similar mechanisms for moving the plunger along the cylinder may be found in U.S. Pat. Nos. 7,144,384; 7,128,727, 6,656,159 and 6,656,158, which patents are incorporated by reference herein for all purposes.

According to other variants, a non-rigid collapsible pouch may be substituted for the rigid-walled cylinder 154 and the plunger 156 shown in FIG. 2. It will be recognized that where the reservoir 152 is in the form of a non-rigid collapsible pouch, a spring-based mechanical system may be used to compress and pressurized the reservoir. According to still further variants, a non-mechanical system may be used to move the plunger 156 or compress the bag. For example, a gas-generating system may be used, including a two-component system wherein the components are kept apart until the gas is to be generated, in which case they are combined. As a further alternative, a swellable gel may be used, wherein the introduction of water from a source internal to the device causes the gel to increase in dimension to move the plunger or compress the pouch. Examples of such alternative mechanisms may be found in U.S. Pat. Nos. 5,957,895; 5,858,001; and 5,814,020, which patents are incorporated by reference herein for all purposes.

Further, the delivery device 50 may include a fill port 160 in fluid communication with the reservoir 152, the fill port 160 having an inlet 162 disposed on the exterior surface 84 of the housing 52 (FIG. 2). The inlet 162 may be adapted to receive a luer tip of a syringe (e.g., syringe 163 illustrated in FIG. 1), although a piercable rubber septum may be used instead, for example. The fill port 160 may also include a cover disposed in the inlet 162 to close the fill port 160. An outlet 164 of the fill port 160 is connected to the reservoir 152. One or more filters may be disposed between the inlet 162 and the outlet 164 to limit the passage of air or particulate matter into the reservoir 152 along with the drug. In use, the healthcare provider may inject the drug from the syringe 163 through the fill port 160 into the reservoir 152, and the syringe 163 may be provided as a pre-filled syringe (filled with any of the materials mentioned above) to the healthcare provider with the delivery device 50 as a kit.

In addition, the drug supply 62 may include a pinch valve 168 or other type of valve disposed between the reservoir 152 and the needle 54 (FIGS. 2 and 3). The inclusion of the valve 168 permits greater control of the timing of the delivery of the drug. Other devices, such as flow regulators, may be disposed in the flow path between the reservoir 152 and the patient to control the flow of the drug therebetween.

A controller 60 is coupled to the injector 56 and the drug supply 62. The controller 60 is configured to control the injector 56 and the drug supply 62 to carry out certain activities. The controller 60 is disposed within the interior space 82 defined within the disposable housing 52 and configured prior to being disposed within the space 82. Thus, once the controller 60 is disposed in the space 82 and the housing 52 is closed (and potentially sealed), the controller 60 may not be reconfigured.

According to one embodiment, the controller 60 may include a programmable microprocessor 180 (FIGS. 2 and 3) and a power supply (not shown) coupled to the microprocessor 180. The power supply may include one or more batteries. Alternatively, the controller 60 may be a mechanical device, a combination of mechanical devices, a combination of electrical devices (hard-wired circuits or circuit components), or a combination of mechanical and electrical devices.

For instance, as noted above, the controller 60 must determine that a preselected time period has elapsed. The controller may be programmed to perform this action by accessing a timer circuit or a timer function within the microprocessor 180. Alternatively, in a mechanical controller, the timer may refer instead to a clockwork mechanism, a spring-driven timer, or a dashpot timer. A benefit of the use of a mechanical controller utilizing a mechanical timer would be the elimination of batteries, making the device more environmentally friendly for purposes of disposal.

A number of different mechanisms or input devices may be used to initiate the operation of the controller 60 so that it carries out its programming, or operates according to its configuration. According to an embodiment of the actuation mechanism, a single button 184 (FIGS. 2 and 3) may be coupled to the controller 60. The button 184 may be disposed so that depends through the exterior surface 84 of the housing 52, and the controller 60 may be responsive to actuation of the button 184 (e.g., depression of the button 184) to initiate the controller program. Alternatively, an input device may be recessed within the housing 52, such that a tool or instrument (such as a pin or key) must be disposed into or through an opening or hole in the exterior surface 84 of the housing 52 so as to actuate the input device.

The controller 60 is programmed to actuate the injector 56 to move the needle 54 from the retracted state to the deployed state only once. The controller 60 is also programmed to determine that a preselected time period has elapsed only once. Further, the controller 60 is programmed to actuate the drug supply to deliver the volume of the drug to the patient as a single bolus.

In particular, the controller 60 may be programmed to determine that a 24-hour period has elapsed after actuation of the device 50 (e.g., by depression of the button 184). Alternatively, the controller 60 may be programmed to determine that a 27-hour period has elapsed after actuation of the device 50. Further, the controller 60 may be programmed to determine that a period of time has elapsed within 24 to 27 hours after actuation of the device 50, e.g., 24, 25, 26, or 27 hours or even fractions thereof, such as 24.5 hours. Additionally, the controller 60 may be programmed to determine that a period of time has elapsed within 22 to 29 hours after actuation of the device 50, e.g., 22, 23, 24, 25, 26, 27, 28 or 29 hours or even fractions thereof, such as 22.5 hours. As a still further alternative, the controller may be programmed to determine that a preselected period has elapsed after actuation of the device 50 lying outside the previously recited ranges. Moreover, it will be understood that to the extent that the controller 60 is programmed to determine that a 24-hour period or at least a 24-hour period, for example, as elapsed, this would include times within a range about 24 hours (e.g., ±10 minutes).

According to certain embodiments, the delivery device 50 may be used in conjunction with a drug or other material (e.g., protein) that is stable over the time period that the controller 60 is programmed to track. For example, the delivery device 50 may be used in conjunction with a drug that is stable for at least 27 hours. Alternatively, the delivery device 50 may be used in conjunction with a drug that is stable for at least 24 to 27 hours. Furthermore, it will be understood that to the extent the delivery device 50 may be used in conjunction with a drug that is stable for at least 24 to 27 hours, this may include an even broader range of stabilities, such as from 21 to 30 hours.

Further, the controller 60 may be programmed to actuate the drug supply 62 to deliver the volume of the drug to the patient as a single bolus in less than thirty minutes. For example, the controller 60 may be programmed to actuate the drug supply to deliver the volume of the drug to the patient as a single bolus in less than ten minutes. In fact, the controller 60 may be programmed to actuate the drug supply 62 to deliver the volume of the drug to the patient as a single bolus in less than six seconds. In an embodiment wherein the drug supply 62 includes a valve 168 (FIGS. 2 and 3), the controller 60 may be programmed to open the valve 168 prior to actuating the remainder of the drug supply 62 to deliver the volume of the drug. Moreover, it will be understood that to the extent the controller 60 delivers the volume in ten minutes, for example, this would include times within a range about 10 minutes (e.g., ±3 minutes). In any event, the delivery of the volume of the drug as a single bolus should be understood to be the same or similar to a single injection of the volume of the drug.

The controller 60 may also be programmed to cause other actions to occur. For example, the controller 60 may be programmed to actuate the injector 56 to move the needle 54 from the deployed state to the retracted state only once.

Additionally, the controller 60 may be coupled to one or more indicators 190, 192 (FIGS. 2 and 3). These indicators 190, 192, which may be visual, audible or even tactile, may be used to signal to the healthcare provider or the patient that the controller 60 is operating according to one or another state. For example, the controller 60 may control the indicator 190, which may be a light emitting diode (LED) for example, to signal the patient that the device 50 has been activated, that the needle 54 is about to be inserted, or that the drug delivery has begun or has been completed. Other possible electrical indicators include buzzers and other noisemakers.

It will be recognized that it is also possible to utilize electromechanical or mechanical indicators. For example, switches or flags may be used, which switches or flags may be initially disposed within the housing in a retracted state and depend from the housing in a deployed state. The switches or flags may depend from the portion of the housing opposite the patient to improve their visibility, or may depend from the portion of the housing facing or proximate to the patient to provide a tactile signal as well as or in substitution for a visual signal. Mechanical devices may also be used, such as ratchets that create an audible "clicking" sound as a toothed wheel or paddle wheel moves past a fixed pawl.

According to still further embodiments of the drug delivery device 50 according to the present disclosure, the device 50 may include a mechanism for cleaning or sterilizing the injection site (i.e., the location where the needle 54 and catheter 120 are inserted into the patient; see FIG. 2). For example, like the shield 134 above, a spring-biased isopropyl alcohol swab may be maintained in the housing 52, the controller 60 activating the swab to move across the opening 130 prior to insertion of the needle 54 and catheter 120. Alternatively, a pressurized supply of sterilizing agent (such as isopropyl alcohol) could be disposed within the housing 52 proximate to the opening 130, and the controller 60 could activate the sterilizing agent supply to spray or otherwise apply an appropriate amount of the sterilizing agent prior to insertion of the needle 54.

Turning then to the use and operation of the device 50, a healthcare provider may obtain an unfilled device according to the above-mentioned disclosure. In its unfilled state, the reservoir 152 (FIG. 2) may be empty, but the controller 60 is already configured to carry out the steps of injecting the needle 54, determining that a preselected time has elapsed, and actuating a drug supply 62 to deliver a volume of drug to the patient. The healthcare provider may then obtain a syringe (e.g., syringe 163) that has been filled with at least the volume of drug that the device will deliver to the patient. The syringe may in fact be filled with more than the volume to be delivered to the patient, and may be pre-filled or may be filled by the healthcare provider by drawing the desire amount from a container, such as a vial, cartridge or bag. The syringe may then be connected to the fill port 160, and the volume of drug injected into the reservoir 152.

The healthcare provider may then remove the disposable sheet 104 from the adhesive layer 100 (FIG. 2), and place the portion 102 of the exterior surface 84 bearing the adhesive layer 100 against the skin of the patient over a desired injection site. The device 50 adheres to the skin of a patient, preferably in such a fashion that the device 50 will not freely detach from the skin until after the volume of drug has been delivered to the patient. The healthcare provider may then activate the controller 60, by depressing the button 184, for example.

As mentioned above, the device 50 automatically injects the pointed end 58 of the needle 54 from the space 82 defined in a housing 52 of the delivery device 50 into the patient only once according to the configuration of the controller 60 contained within the space 82 (FIGS. 5 to 8). According to certain embodiments, the needle 54 may be inserted into the patient at the time the controller 60 is activated. One benefit of the device 50 operating in this fashion is that there may be a greater assurance of injection site sterility, assuming that the skin is cleaned with a sterilizing agent (e.g., isopropyl alcohol) immediately prior to application of the device 50. According to other embodiments, the needle 54 is not inserted into the patient until the preselected time has elapsed. In any event, the controller 60 may activate one or more indicators 190, 192 (FIG. 2) to provide a visual, audible or tactile signal that the device 50 has been activated, and if the needle 54 is not inserted into the patient at this time, a further visual, audible or tactile signal may be provided immediately before the delayed insertion of the needle 54.

The device 50 then automatically determines when a preselected time period has elapsed. The device 50 does this only once according to the configuration of the controller 60, the controller 60 being configured to determine the preselected time before the controller 60 is disposed in the space 82. The time period may vary according to the circumstances of the particular application, although the configuration of the device 50 in this regard may not be altered according to the healthcare provider or the patient. Where the needle 54 has already been inserted into the patient, the delivery of the drug may be accompanied by a visual or audible indication to the patient that the drug delivery is imminent.

The device 50 then automatically actuates the drug supply 62 to deliver a volume of a drug to the patient as a single bolus via the needle 54 according to the configuration of the controller 60 contained within the space 82 (FIGS. 5 to 8). Dependent upon structure of the drug supply 62 used, the controller 60 may open the valve 168 and initiate the pump 150 to effectively pressurize the reservoir 152 and administer the drug to the patient. The delivery of the drug may be accompanied by a still further visual or audible indication that the drug delivery is occurring. According to certain embodiments, the visual or audible indication may be maintained until the drug delivery is complete; according to other embodiments, the indication may occur discretely at the beginning and the end of the delivery process.

When the delivery of the drug is complete, which may be determined by the controller 60 with reference to an air detector or sensor, the controller may close the valve 168 (FIGS. 2 and 3) to stop the delivery process. The controller 60 may also cause the injector 56 to move the needle 54 from the deployed state to the retracted state. After the valve 168 is closed and the needle 54 is withdrawn, the controller 60 may control an indicator 190, 192 to provide a visual or audible signal that the process is complete and the needle 54 is withdrawn. The patient may then remove the device from the skin, and dispose of the device 50 in an appropriate medical waste container.

In addition to this general process, the device 50 may include other suboperations. For example, according to certain embodiments, the device 50 may automatically retract the pointed end of the needle 54 into the space 82 (FIGS. 5 and 7) only once according to the configuration of the controller 60 contained within the interior space. Also, as mentioned above, the device 50 may automatically determine that a preselected time period has elapsed comprises automatically determining that a twenty-four hour period has elapsed.

As will be recognized, the devices according to the present disclosure may have one or more advantages relative to conventional technology, any one or more of which may be present in a particular embodiment in accordance with the features of the present disclosure included in that embodiment. Other advantages not specifically listed herein may also be recognized as well.

We claim:

1. A drug delivery device comprising:
   a disposable housing having an interior surface defining an interior space, and an exterior surface;
   a needle having a retracted state wherein the needle is withdrawn inside of the interior space and a deployed state wherein a pointed end of the needle projects beyond the exterior surface of the housing;
   an injector coupled to the needle to move the needle between the retracted and deployed states;
   a reservoir disposed within the interior space, the reservoir configured to receive a volume of a drug and to be in fluid communication with the needle; and
   a controller coupled to the injector and the reservoir, the controller being configured to actuate the injector to move the needle from the retracted state to the deployed state only once, to only once determine when a preselected time period has elapsed after initiation of action of the controller, and to actuate the reservoir to deliver the volume of the drug to the patient as a single bolus after the preselected time period has elapsed after the initiation of the action of the controller, the controller disposed within the interior space and configured prior to being disposed within the interior space,
   wherein the delivery device is wearable, disposable, and single-use.

2. The delivery device according to claim 1, further comprising a volume of an erythropoiesis stimulating agent disposed in the reservoir.

3. The delivery device according to claim 1, further comprising a volume of a granulocyte colony-stimulating factor disposed in the reservoir.

4. The delivery device according to claim 1, further comprising a volume of a TNF blocker disposed in the reservoir.

5. The delivery device according to claim 1, further comprising a volume of a pegylated granulocyte colony-stimulating factor disposed in the reservoir.

6. The delivery device according to claim 1, further comprising a volume of interleukin-receptor specific antibody disposed in the reservoir.

7. The delivery device according to claim 1, further comprising a volume of IGF-receptor specific antibody disposed in the reservoir.

8. The delivery device according to claim 1, further comprising a volume of TGF-specific antibody disposed in the reservoir.

9. The delivery device according to claim 1, wherein the controller determines that the preselected time period has elapsed.

10. The delivery device according to claim 9, wherein the controller determines that at least a 24-hour period has elapsed after actuation of an input device.

11. The delivery device according to claim 1, wherein the controller is configured to actuate the reservoir to deliver the volume of the drug to the patient as a single bolus in less than thirty minutes.

12. The delivery device according to claim 11, wherein the controller is configured to actuate the reservoir to deliver the volume of the drug to the patient as a single bolus in less than six seconds.

13. The delivery device according to claim 1, wherein the controller is configured to actuate the injector to move the needle from the deployed state to the retracted state only once.

14. The delivery device according to claim 1, comprising an input device coupled to the controller, the controller responsive to actuation of the input device to initiate action of the controller.

15. The delivery device according to claim 1, wherein the controller comprises a microprocessor programmed to actuate the injector and to actuate the reservoir.

16. The delivery device according to claim 1, further comprising a pump, wherein the controller actuates the pump to move the volume of drug from the reservoir to the needle.

17. The delivery device according to claim 16, further comprising a pinch valve disposed between the pump and the needle, wherein the controller opens the pinch valve prior to actuating the pump.

18. The delivery device according to claim 1, wherein the interior space is a sealed space.

19. The delivery device according to claim 1, further comprising an adhesive adapted to releasably secure the housing to skin during a single application, the adhesive disposed on a portion of the exterior surface and covered with a removable, disposable sheet prior to application of the housing to the skin of a patient.

20. The delivery device according to claim 1, comprising a fill port in fluid communication with the reservoir, the fill port having an inlet disposed on the exterior surface of the housing.

21. A kit comprising a delivery device according to claim 1, in combination with a syringe.

22. The delivery device according to claim 10, wherein the at least 24-hour period is 25, 26, 27, 28 or 29 hours or a fraction thereof.

23. The delivery device according to claim 22, wherein the at least 24-hour period is 27 hours or a fraction thereof.

24. The delivery device according to claim 9, wherein the controller determines that 22 or 23 hours has elapsed.

25. The drug delivery device of claim 1, comprising a catheter or soft cannula surrounding the needle and movable together with the needle.

26. The drug delivery device of claim 1, the controller being configured to actuate the injector to move the needle from the retracted state to the deployed state upon initiation of the action of the controller such that the preselected time period begins when the injector is actuated to move the needle from the retracted state to the deployed state.

27. A method of operation of a wearable, disposable, single-use drug delivery device, the method comprising:
    initiating a controller contained within an interior space defined by a housing of the delivery device;
    automatically injecting a pointed end of a needle from the interior space into the patient to define an injection site only once according to the controller;
    determining, only once with the controller, when a preselected time period has elapsed after initiation of the controller; and
    automatically actuating a reservoir to deliver a volume of a drug to the patient through the injection site as a single bolus after the preselected time period has been determined to have elapsed according to the controller.

28. The method according to claim 27, wherein the drug comprises an erythropoiesis stimulating agent.

29. The method according to claim 27, wherein the drug comprises a granulocyte colony-stimulating factor.

30. The method according to claim 27, wherein the drug comprises a TNF blocker.

31. The method according to claim 27, wherein the drug comprises a pegylated granulocyte colony-stimulating factor.

32. The method according to claim 27, wherein the drug comprises interleukin-receptor specific antibody.

33. The method according to claim 27, wherein the drug comprises IGF-receptor specific antibody.

34. The method according to claim 27, wherein the drug comprises TGF-specific antibody.

35. The method according to claim 27, further comprising automatically determining that the preselected time period has elapsed according to the controller contained within the interior space, the controller being configured to determine the preselected time period before the controller is disposed in the interior space.

36. The method according to claim 35, wherein the preselected time period is at least a 24-hour period.

37. The method according to claim 27, comprising automatically retracting the pointed end of the needle into the interior space only once according to the configuration of the controller contained within the interior space.

38. The method of claim 27, comprising inserting a catheter or soft cannula into subcutaneous tissue of the patient with the needle.

39. The method according to claim 27, wherein automatically injecting the pointed end of a needle comprises automatically injecting the needle with an injector configured to move the needle, the injector being enclosed entirely within the interior space defined by the housing and fixed relative to the housing.

40. The method of claim 27, comprising automatically injecting the pointed end of the needle into the patient upon initiation of the controller such that the preselected time period begins when the pointed end of the needle is injected into the patient.

41. A wearable, single-use drug delivery device comprising:
    a disposable housing having an interior surface and an exterior surface, the interior surface defining an interior space;
    a needle movable between a retracted position where the needle is withdrawn inside of the interior space of the housing and a deployed position where a pointed end of the needle projects from the exterior surface of the housing;
    a catheter or soft cannula surrounding the needle;
    an injector enclosed within the interior space of the housing and configured to move the needle between the retracted position and the deployed position;
    a reservoir enclosed within the interior space of the housing and in fluid communication with the needle, the reservoir being configured to receive a volume of a drug; and
    a controller operatively connected to the injector and the reservoir, the controller being configured to only once: (i) actuate the injector to move the needle from the retracted position to the deployed position, (ii) insert the catheter or soft cannula into subcutaneous tissue of a patient, (iii) move the needle from the deployed position to the retracted position, (iv) determine when a preselected time period has elapsed after actuation of the injector to move the needle from the retracted position to the deployed position, and (v) actuate the reservoir to deliver the volume of the drug to the patient via the needle as a single bolus.

42. The wearable, single-use drug delivery device of claim 41, the injector being fixed relative to the housing.

* * * * *